(12) United States Patent
Will et al.

(10) Patent No.: US 9,238,832 B2
(45) Date of Patent: *Jan. 19, 2016

(54) ALLELE-SPECIFIC AMPLIFICATION OF NUCLEIC ACIDS

(75) Inventors: Stephen Will, Cham (CH); Alison Tsan, Castro Valley, CA (US); Nicolas Newton, Oakland, CA (US)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 481 days.

This patent is subject to a terminal disclaimer.

(21) Appl. No.: 12/962,861

(22) Filed: Dec. 8, 2010

(65) Prior Publication Data

US 2011/0311968 A1 Dec. 22, 2011

Related U.S. Application Data

(60) Provisional application No. 61/285,690, filed on Dec. 11, 2009.

(51) Int. Cl.
  *C12P 19/34* (2006.01)
  *C12Q 1/68* (2006.01)

(52) U.S. Cl.
  CPC ............ *C12Q 1/6858* (2013.01); *C12Q 1/6886* (2013.01); *C12Q 2600/156* (2013.01); *C12Q 2600/166* (2013.01)

(58) Field of Classification Search
  USPC .................................... 435/6.12, 91.1, 91.2
  See application file for complete search history.

(56) References Cited

U.S. PATENT DOCUMENTS

| | | | |
|---|---|---|---|
| 5,137,806 A | 8/1992 | Le Maistre et al. | |
| 5,210,015 A | 5/1993 | Gelfand et al. | |
| 5,521,301 A | 5/1996 | Wallace et al. | |
| 5,595,890 A | 1/1997 | Newton et al. | |
| 5,639,611 A | 6/1997 | Wallace et al. | |
| 5,990,303 A | 11/1999 | Seela | |
| 6,001,611 A | 12/1999 | Will | |
| 7,135,291 B2 | 11/2006 | Sagawa et al. | |
| 7,408,051 B2 | 8/2008 | Ma et al. | |
| 2003/0108900 A1* | 6/2003 | Oliphant et al. | 435/6 |
| 2005/0019918 A1* | 1/2005 | Sumimoto et al. | 435/375 |
| 2006/0078928 A1* | 4/2006 | Ankenbauer et al. | 435/6 |
| 2006/0115844 A1* | 6/2006 | Finkelstein et al. | 435/6 |
| 2006/0246476 A1 | 11/2006 | Polsky et al. | |
| 2007/0117118 A1 | 5/2007 | Yuku et al. | |
| 2010/0099110 A1 | 4/2010 | Will et al. | |

FOREIGN PATENT DOCUMENTS

| | | |
|---|---|---|
| EP | 1241266 A1 | 9/2002 |
| EP | 0974672 B1 | 4/2003 |
| WO | 0043544 A1 | 7/2000 |
| WO | 03072814 A2 | 9/2003 |
| WO | 03072814 A3 | 9/2003 |
| WO | 2007127992 A2 | 11/2007 |
| WO | 2007127992 A3 | 11/2007 |
| WO | EP2009007463 | 2/2010 |
| WO | 2010046067 | 4/2010 |
| WO | 2010046067 A1 | 4/2010 |
| WO | 2010046067 A9 | 4/2010 |
| WO | EP2010007560 | 2/2011 |
| WO | EP2010007560 | 3/2012 |

OTHER PUBLICATIONS

The nucleic acid sequence search reports for SEQ ID No. 11 (AC. AEI01576) and SEQ ID No. 2 (AC. ADW27069) searched Nov. 29, 2012.*
Lowe et al. Nucleic acid research, 1990,,vol. 18(7), p. 1757-1761.*
Witcombe, David, et al., 1999, "Detection of PCR products using self-probing amplicons and fluorescence", Nature Biotechnology, 17:804-807.
Andre, Paulo, et al., 1997, "Fidelity and Mutational Spectrum of Pfu DNA Polymerase on a Human Mitochondrial DNA Sequence", Genome Res., 7:843-852.
Applied Biosystems, 2009, "Avoiding DNA Contamination in RT-PCR (Technical Bulletin #176)", http//www.ambion.com/techlib/tb/tb_176.html.
Figalgo De Silva, Elizabeth, et al., 2007, "DNA polymerase proofreading: active site switching catalyzed by the bacteriophage T4 DNA polymerase", Nucleic Acids Research, 35(16):5452-5463.
Gaster, Jens, et al., 2005, "Tuning Single Nucleotide Discrimination in Polymerase Chain Reactions (PCRs): Synthesis of Primer Probes Bearing Polar 4'-C-Modifications and Their Application in Allele-Specific PCR", Chemistry: a European Journal, 11:1861-1870.
Goodman, Myron F., et al., 1993, "Biochemical Basis of DNA Replicon Fidelity", Critical Reviews in Biochemistry and Molecular Biology, 28(2):83-126.
Newton, C. R., et al., 1989, "Analysis of any point mutation in DNA. The amplification refractory mutation system (ARMS)", Nucleic Acids Research, 17(7):2503-2516.
Reddy, Michael K., et al., 1992, "Processive Proofreading is Intrinsic to T4 DNA Polymerase", The Journal of Biological Chemistry, 267(20):14157-14166.
Strerath, M. et al., 2007, "Modified Oligonucleotides as Tools for Allele-Specific Amplification", Methods Mol Biol. , 402:317-28.
Tews, B. et al., 2003, "Application of the C4'-alkylated deoxyribose primer system (CAPS) in allele-specific real-time PCR for increased selectivity in discrimination of single nucleotide sequence variants", Biol Chem., 384 (10-11):1533-41.
Tindall, Kenneth R., et al., 1988, "Fidelity of DNA Synthesis by the Thermus aquaticus DNA Polymerase", Biochemistry 27:6008-6013.

* cited by examiner

*Primary Examiner* — Kenneth R. Horlick
*Assistant Examiner* — Joyce Tung
(74) *Attorney, Agent, or Firm* — David J. Chang

(57) ABSTRACT

The present invention includes a method of allele-specific amplification, utilizing an allele-specific oligonucleotide, at least partially complementary to more than one variant of the target sequence, having an internally-placed selective nucleotide complementary to only one variant of the target sequence wherein the allele-specific oligonucleotide is extended by a nucleic acid polymerase predominantly or exclusively when hybridized to the variant of the target sequence for which it has said complementary selective nucleotide.

16 Claims, 7 Drawing Sheets

SCORPION ARMS (UNI-MOLECULAR, CLOSED FORMAT)

SCORPION,
UNBOUND,
RANDOM COIL:

SCORPION,
BOUND:

ALLELE-SPECIFIC AMPLIFICATION OF NUCLEIC ACIDS

CROSS REFERENCE TO RELATED INVENTION

This application claims the benefit of priority of U.S. Provisional patent application Ser. No. 61/285,690, filed Dec. 11, 2009, which is incorporated herein by reference in its entirety.

REFERENCE TO SEQUENCE LISTING

This application contains a Sequence Listing submitted as an electronic text file named "26248US1.txt", having a size in bytes of 7 kb, and created on Dec. 1, 2010. The information contained in this electronic file is hereby incorporated by reference in its entirety pursuant to 37 CFR §1.52(e)(5).

FIELD OF THE INVENTION

The invention relates to the field of nucleic acid amplification and specifically to the field of allele-specific amplification.

BACKGROUND OF THE INVENTION

Allele-specific amplification of nucleic acids allows for simultaneous amplification and analysis of the target sequence. Allele-specific amplification is commonly used when the target nucleic acid has one or more variations (polymorphisms) in its sequence. Nucleic acid polymorphisms are used in DNA profile analysis (forensics, paternity testing, tissue typing for organ transplants), genetic mapping, distinguishing between pathogenic strains of microorganisms as well as detection of rare mutations, such as those occurring in cancer cells, existing in the background of cells with normal DNA.

In a successful allele-specific amplification, the desired variant of the target nucleic acid is amplified, while the other variants are not, at least not to a detectable level. A typical allele-specific amplification assay involves a polymerase chain reaction (PCR) with at least one allele-specific primer designed such that primer extension occurs only when the primer forms a hybrid with the desired variant of the target sequence. When the primer hybridizes to an undesired variant of the target sequence, primer extension is inhibited.

Many ways of enhancing allele-specificity of primers have been proposed. However, for many clinically-relevant nucleic acid targets lack of specificity of PCR remains a problem. Therefore radically novel approaches to design of allele-specific primers are necessary.

SUMMARY OF THE INVENTION

In a first aspect, the invention relates to a method of allele-specific amplification of a variant of a target sequence, the target existing in the form of several variant sequences, the method comprising
(a) hybridizing a first and a second oligonucleotides to at least one variant of the target sequence; wherein the first oligonucleotide is at least partially complementary to one or more variants of the target sequence, and the second oligonucleotide is at least partially complementary to one or more variants of the target sequence, and has at least one internal selective nucleotide complementary to only one variant of the target sequence;
(b) extending the second oligonucleotide with a nucleic acid polymerase, wherein said polymerase is capable of extending said second oligonucleotide preferentially when said selective nucleotide forms a base pair with the target, and substantially less when said selective nucleotide does not form a base pair with the target.

In a second aspect, the invention relates to a method of detecting a variant of a target sequence, the target existing in the form of several variant sequences, the method comprising
(a) hybridizing a first and second oligonucleotides to at least one variant of the target sequence; wherein said first oligonucleotide is at least partially complementary to one or more variants of the target sequence and said second oligonucleotide is at least partially complementary to one or more variants of the target sequence, and has at least one internal selective nucleotide complementary to only one variant of the target sequence;
(b) extending the second oligonucleotide with a nucleic acid polymerase; wherein said polymerase is capable of extending said second oligonucleotide preferentially when said selective nucleotide forms a base pair with the target, and substantially less when said selective nucleotide does not form a base pair with the target; and
(c) detecting the products of said oligonucleotide extension, wherein the extension signifies the presence of the variant of a target sequence to which the oligonucleotide has a complementary selective nucleotide.

In a third aspect, the invention relates to a kit for allele-specific amplification of a target sequence, said target existing in the form of several variant sequences, the kit comprising
(a) a first oligonucleotide, at least partially complementary to one or more variant of the target sequence; and
(b) a second oligonucleotide, at least partially complementary to one or more variants of the target sequence having at least one internal selective nucleotide complementary to only one variant of the target sequence.

In a fourth aspect, the invention relates to an oligonucleotide for performing an allele-specific amplification of a target sequence, said target existing in the form of several variant sequences, the oligonucleotide comprising
(a) a sequence at least partially complementary to a portion of one or more variants of said target sequence;
(b) at least one internal selective nucleotide complementary to only one variant of the target sequence.

In a fifth aspect, the invention relates to a reaction mixture for allele-specific amplification of a target sequence, said target existing in the form of several variant sequences, the mixture comprising
(a) a first oligonucleotide, at least partially complementary to one or more variant of the target sequence; and
(b) a second oligonucleotide, at least partially complementary to one or more variants of the target sequence but having at least one internal selective nucleotide complementary to only one variant of the target sequence.

DETAILED DESCRIPTION OF THE INVENTION

Definitions

Figure 1:
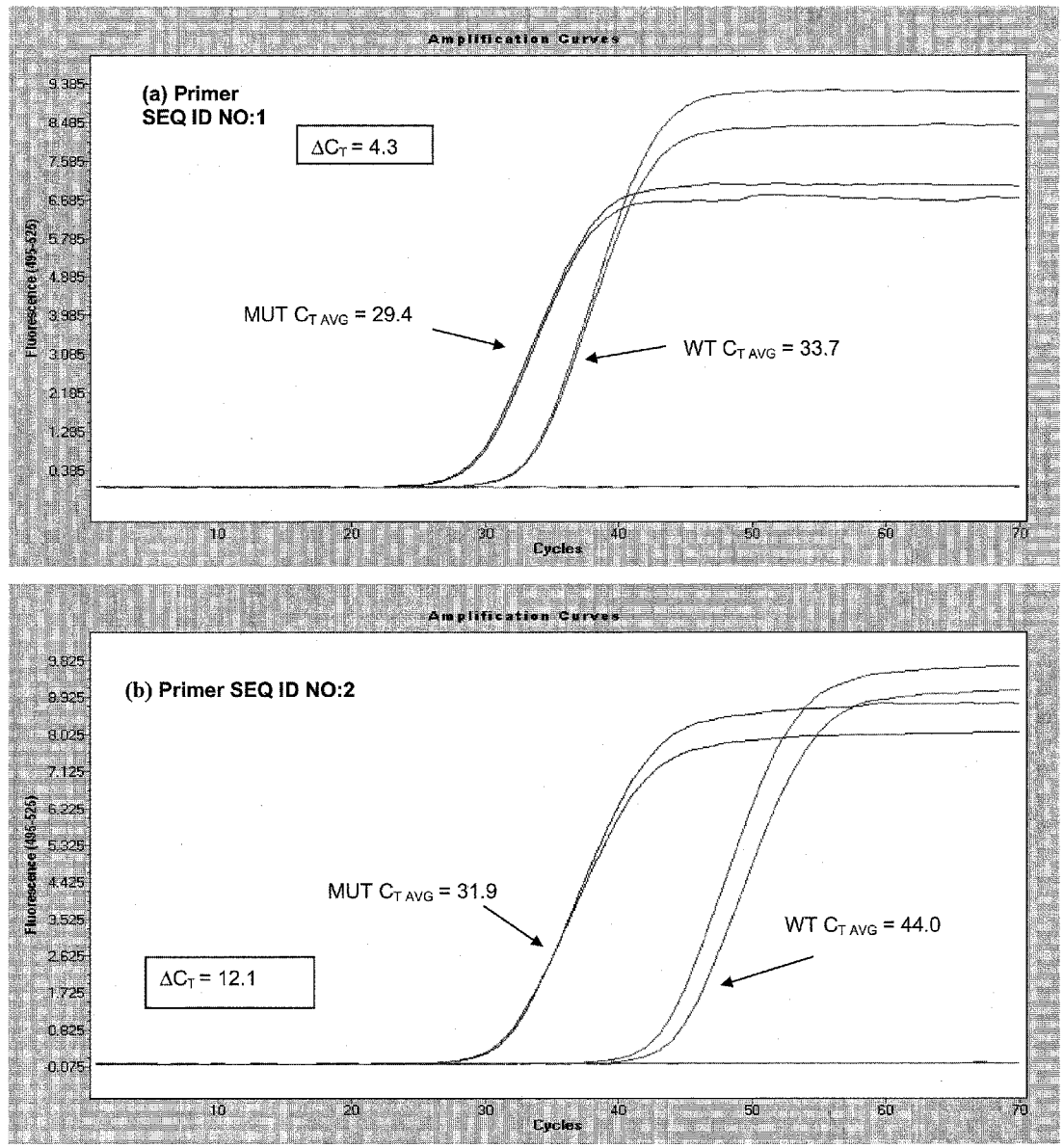
FIG. 1 shows the results of allele-specific amplification using various nucleic acid polymerases and primers with internal selective nucleotide according to the present invention.

Unless defined otherwise, all technical and scientific terms used herein have the same meaning as commonly understood by one of ordinary skill in the art to which this invention pertains. In describing and claiming the present invention, the following definitions will be used.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49(10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphosphoroamidite linkages (seg Eckstein, Oligonucleotides and Analogues: a Practical Approach, Oxford University Press (1992)), and peptide nucleic acid backbones and linkages (see, Egholm (1992) J. Am. Chem. Soc. 114:1895). These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Hely. Chim. Acta 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "template nucleic acid", "template" or "target" refers to a nucleic acid of interest to which a primer can hybridize and be extended under suitable conditions. In the context of nucleic acid amplification, "target" is preferably a region of nucleic acid, consisting of sequences at least partially complementary to at least two primer sequences, and an intervening sequence. (If the target is a single stranded nucleic acid, it consists of a sequence at least partially complementary to one primer and a sequence at least partially identical to the second primer.) Template nucleic acids can exist as isolated nucleic acid fragments or be a part of a larger nucleic acid fragment. Target nucleic acids can be derived or isolated from essentially any source, such as cultured microorganisms, uncultured microorganisms, complex biological mixtures, tissues, sera, ancient or preserved tissues or samples, environmental isolates or the like. Further, template nucleic acids optionally include or are derived from cDNA, RNA, genomic DNA, cloned genomic DNA, genomic DNA libraries, enzymatically fragmented DNA or RNA, chemically fragmented DNA or RNA, physically fragmented DNA or RNA, or the like. Template nucleic acids can also be chemically synthesized using techniques known in the art.

An "oligonucleotide" refers to a nucleic acid polymer that includes at least two, but typically 5-50 nucleotides and more typically, between 15 and 35 nucleotides. Oligonucleotides may be prepared by any suitable method known in the art, including, for example, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103:3185-3191; automated synthesis methods; the solid support method of U.S. Pat. No. 4,458,066 or any other chemical method known in the art.

A "primer" is an oligonucleotide that can hybridize to a template nucleic acid and permit chain extension or elongation using a nucleotide polymerase. Although other primer lengths are sometimes utilized, primers typically range from 15 to 35 nucleotides. Short primers generally form sufficiently stable hybrids with template nucleic acids at cooler temperatures. A primer need not be perfectly complementary to the template nucleic acids for the extension to occur. A primer that is at least partially complementary to the template nucleic acid is typically capable of hybridizing with the template nucleic acid for extension to occur. A primer nucleic acid can be labeled, if desired, by incorporating a label detectable by radiological, spectroscopic, photochemical, biochemical, immunochemical, or chemical techniques.

An "allele-specific primer" is a primer that can hybridize to several variants of the template nucleic acid, but permit elongation by the polymerase when hybridized, with only some of the variants of the template nucleic acid. With other variants of the template nucleic acid the primer-template hybrid may not be extended or is extended less efficiently by the polymerase.

Nucleic acids are "extended" or "elongated" when additional nucleotides are incorporated into the nucleic acids, for example by a nucleotide incorporating biocatalyst, at the 3' end of a nucleic acid.

An amplification assay is "selective" or "allele-selective" if it yields predominance (i.e., a majority but less than 100%) of one product over other possible products. An assay is described as "allele-selective" as long as amplification of the undesired (mismatched) variant of the target sequence is detectable. The term "specific" or "allele-specific" with respect to amplification assay is used if one of the possible products is formed exclusively. An assay where amplification of the undesired target is undetectable is called "allele-specific." However, it is understood that as the methods of detection become more sensitive, some assays previously known to be allele-specific, turn out to be allele-selective, i.e. some amplification of undesired variants of the target becomes detectable. Therefore, in the context of this invention, the term "allele-specific" is meant to encompass both strictly allele-specific, as well as allele-selective amplification.

A "genotype" refers to all or part of the genetic constitution of a cell or subject, or group of cells or subjects. For example, a genotype includes the particular mutations and/or alleles (e.g., polymorphisms, such as single nucleotide polymorphisms (SNPs) or the like) present at a given locus or distributed in a genome.

A "nucleic acid polymerase" refers to an enzyme that catalyzes the incorporation of nucleotides into a nucleic acid. Exemplary nucleic acid polymerases include DNA polymerases, RNA polymerases, terminal transferases, reverse transcriptases, telomerases and the like.

A "thermostable enzyme" refers to an enzyme that is stable (i.e., resists breakdown or denaturation) and retains sufficient catalytic activity when subjected to elevated temperatures for selected periods of time. For example, a thermostable polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase, is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" enzyme refers to an enzyme comprising an amino acid polymer in which at least one monomer differs from the reference sequence, such as a native or wild-type form of the enzyme. Exemplary modifications include monomer insertions, deletions, and substitutions. Modified enzymes also include chimeric enzymes that have identifiable component sequences (e.g., structural or functional domains, etc.) derived from two or more parent enzymes. Also included within the definition of modified enzymes are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

The term "3' to 5' nuclease activity" or "3'-5' nuclease activity" or "proof-reading activity" refers to an activity of a nucleic acid polymerase, whereby nucleotides are removed from the 3' end of the nucleic acid strand. For example, *E. coli* DNA polymerase III has this activity, whereas the *Thermus aquaticus* (Taq) DNA polymerase does not.

A "label" refers to a moiety attached (covalently or non-covalently), to a molecule and capable of providing information about the molecule. Exemplary labels include fluorescent labels, colorimetric labels, chemiluminescent labels, bioluminescent labels, radioactive labels, mass-modifying groups, antibodies, antigens, biotin, haptens, and enzymes (including peroxidase, phosphatase, etc.).

A "fidelity" or "replication fidelity" is the ability of a nucleic acid polymerase to incorporate a correct nucleotide during template-dependent polymerization. In the context of replication fidelity, "correct nucleotide" on the nascent nucleotide strand is the nucleotide paired with the template nucleotide via Watson-Crick base pairing. Replication fidelity of a particular polymerase results from a combination of incorporating correct nucleotides and removing incorrect nucleotides from the 3'-terminus of the nascent nucleotide strand via the 3'-5' nuclease activity of the polymerase. Various methods of measuring fidelity of a nucleotide polymerase are reviewed in Tindall et al. (1988) Fidelity of DNA synthesis by the *Thermus aquaticus* DNA polymerase. Biochemistry, 27:6008-6013. Typically, polymerases with 3'-5' nuclease (proofreading) capability have higher fidelity than polymerases without the proof-reading activity.

A "hot start", in the context of a nucleic acid amplification reaction, refers to a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol.

A "selective nucleotide" is a nucleotide in an allele-specific primer that confers allele selectivity to the primer. The selective nucleotide is complementary to a corresponding nucleotide in the desired variant of the target nucleic acids but not complementary to the corresponding nucleotide in the undesired variants of the target nucleic acid. In a primer, more than one nucleotide may be complementary to a nucleotide in the desired variants of the target nucleic acids but not complementary to the corresponding nucleotide in the undesired variants of the target nucleic acid. However, the selective nucleotide is located at a position within the primer that affects the specificity of the primer. The selective nucleotide permits efficient or inefficient amplification of the target nucleic acid, depending on whether or not it finds or does not find a complementary partner in the target nucleic acid. A primer may contain more than one selective nucleotide.

A "Watson-Crick base pairing" or simply "base pairing" refers to "conventional" hydrogen bonding within a double-stranded nucleic acid molecule. Watson-Crick base pairing is hydrogen bonding between complementary bases, such as bonding between adenine and thymine, between guanine and cytosine, between adenine and uracil, and between analogs of these bases.

Figure 4:
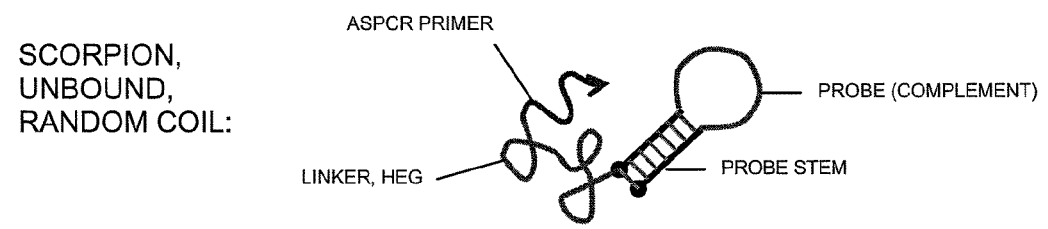
FIG. 4 shows a schematic representation of the structure of a scorpion ARMS format that can be used according to the invention.
Figure 4:
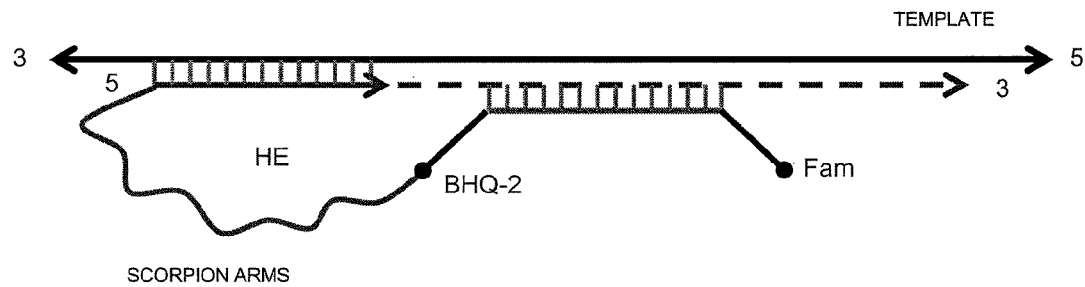

The terms "scorpion", "scorpion-like" or "Scorpion ARMS-like" as used herein denote unimolecular primer-probe combination as described in Whitcombe et al., (1999). Detection of PCR products using self-probing amplicons and fluorescence, Nature Biotech. 17:804-807. Scorpion or scorpion-like primers within the meaning of the present invention incorporate the typical elements of the scorpion, namely a probe portion, a stem loop portion and a primer portion. An example of "scorpion" or "scorpion-like" unimolecular primer-probe format is illustrated in FIG. 4.

The term "internal" as used herein, for example in the expression "a second oligonucleotide, at least partially complementary to one or more variants of the target sequence, but having at least one internal selective nucleotide complementary to only one variant of the target sequence" denotes any nucleotide other than the 3' terminal, for example 1 to 5 nucleotides internally of the 3'-end.

The expression "wherein said polymerase is capable of extending said second oligonucleotide preferentially when said selective nucleotide forms a base pair with the target, and substantially less when said selective nucleotide does not form a base pair with the target" means that extension of the second oligonucleotide by the polymerase is more efficient when the selective nucleotide forms a base pair with the target, than when said selective nucleotide does not form a base pair with the target. This can for example be measured or quantified with the material and methods described in example 1, the results of which are shown on FIG. 1.

The present invention teaches a new allele-specific amplification primer, a method of designing such primer, a method of using the primer in allele-specific amplification a reaction mixture and a kit including the primer. The method of designing the primer may be used alone or in conjunction with existing methods of designing allele-specific primers. A typical allele-specific primer is designed to hybridize to a polymorphic region of the target sequence and contain at least one selective nucleotide, i.e. nucleotide complementary to the desired variants of the polymorphic nucleotide in the target and non-complementary to the undesired variants of the target. Traditionally it was considered necessary to place the selective nucleotide at the 3'-end of the primer, because the terminal mismatch was thought to be a necessary prerequisite for allele-specific amplification. See Newton et al. (1989) Analysis of any point mutation in DNA. The amplification refractory mutation system (ARMS). Nucl. Acids Res. 17:2503-2516.

The present inventors have discovered that internal placement of the selective nucleotide is sufficient to ensure allele-specificity of the primer. The terminal mismatch is not required to confer specificity upon the primer. A sole internal mismatch is sufficient to inhibit extension of the mismatched primer by a nucleotide polymerase. According to the present invention, the selective nucleotide is placed internally of the 3'-end of the primer, between 1 and 5 nucleotides internally of the 3'-end. When the internal nucleotide is mismatched, the undesired, mismatched template is not amplified or amplified less efficiently, while the desired, matched template is amplified efficiently.

In one embodiment, the invention is an oligonucleotide (primer) for use in allele-specific PCR. The primer of the invention comprises 10-50, more preferably 15-35 nucleotides, the majority of them complementary to a sequence in more then one variant of the target sequence. The primer also contains at least one internal selective nucleotide complementary to only one variant of the target sequence.

In some embodiments, the allele-specific primer further contains one or more nucleotides with chemical modifications that further increase its specificity. For example, modifications at the exocyclic amine of a nucleobase have been described in U.S. Pat. No. 6,001,611. The allele specific primer according to the present invention may have a modification at the exocyclic amine of one or more nucleobases. In some embodiments, the modified-base nucleotide occurs between 1 and 5, but preferably 3 nucleotides upstream of the 3'-terminal nucleotide. In other embodiments, the modified-base nucleotide is the 3'-terminal nucleotide. In some embodiments, the modified-base nucleotide occurs both at the 3'-terminus as well as elsewhere within the oligonucleotide primer. In yet other embodiments, the modification may be placed on the selective nucleotide within the allele-specific primer.

According to the present invention, a suitable modification of the exocyclic amino group may be selected based on the presence of the following properties: (1) the modification interferes with but does not prevent Watson-Crick base pairing of the modified base with the complementary base in the double-stranded nucleic acid; (2) the modification interferes with but does not prevent the extension of the primer containing the modified base by the nucleic acid polymerase; (3) the modification allows synthesis of the strand complementary to the strand incorporating the modified base; and (4) the modification increases selectivity of a primer incorporating the modification.

The examples of exocyclic amino groups include the amino groups in the 6-position of adenosine, 2-position of guanosine and 4-position of cytidine. Exocyclic amino groups that take part in base pairing with the complementary nucleic acid strand may also occur in various unconventional nitrogenous bases in nucleotides. Examples of nucleosides with unconventional bases include, without limitation, 3-methyladenosine, 7-methylguanosine, 3-methylguanosine, 5-methylcytidine, and 5-hydroxymethylcytidine. Suitable modifications of exocyclic amino groups of such unconventional bases may also be selected according to the empirical method of the present invention.

The structures of the modified nucleotides containing a modified adenine, guanine, and cytosine base, respectively, are shown below,

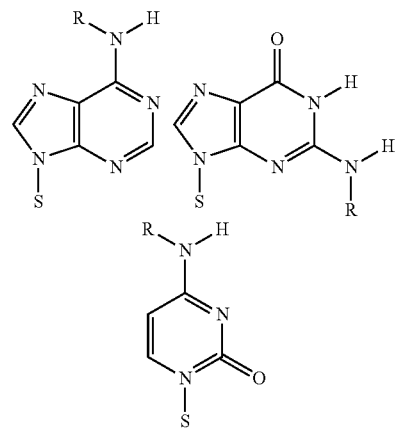

where S represents the sugar moiety, and R represents the modifier group. A variety of modifier groups are envisioned which possess the four properties outlined above. In certain embodiments, modifier groups have the structure:

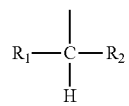

wherein $R_1$ and $R_2$ are independently selected from the group consisting of hydrogen, alkyl, alkoxy, unsubstituted or substituted aryl and phenoxy.

Alkyl groups may be branched or unbranched

Alkyl groups can be $C_1$-$C_{20}$ alkyls, in particular $C_1$-$C_{10}$ alkyls.

Alkoxy groups can be $C_1$-$C_{20}$ alkoxy, in particular $C_1$-$C_{10}$ alkoxy.

Aryl can be unsubstituted or substituted phenyl or naphtyl.

In one embodiment, R is a benzyl group or a substituted benzyl group. In certain embodiments, substituted benzyl groups can have the following structure:

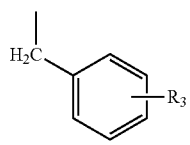

wherein $R_3$ represents a $C_1$-$C_6$ branched or unbranched alkyl group, more preferably a $C_1$-$C_4$ branched or unbranched alkyl group, an alkoxy group, or a nitro group. Preferably, $R_3$ is attached in the para-position.

In some embodiments, the modifier groups are represented by structures shown below:

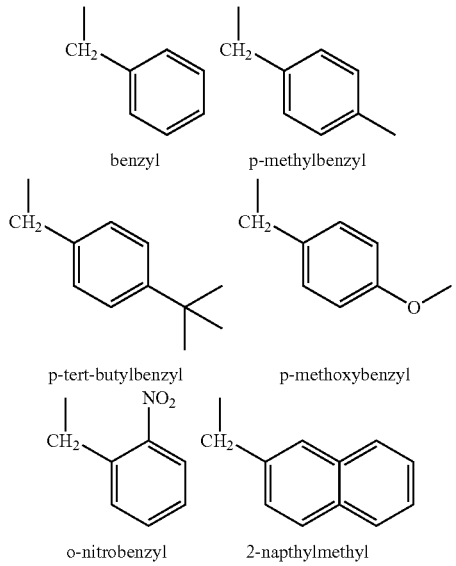

In general, empirical selection of a particular suitable modifier group from the class of compounds described herein can be carried out routinely by one of skill in the art, based on the presence of the four properties listed above. Preferably, suitability of a particular group is determined empirically by using the primers with modified nucleotides in an allele-specific amplification reaction. The suitability of the modification is indicated by the increased selectivity of the reaction utilizing a primer with the base modification, when compared to an identical reaction with an unmodified primer.

Additional mismatches between the primer and the template further destabilize the hybrid between the primer and the undesired variant of the target sequence. The method for optimizing the design of the allele-specific primers can be found in Newton et al. (1989) supra.

The allele-specific primer of the present invention may incorporate various aspects of primer design known in the art. For example, the primer may take the form of a unimolecular primer-probe combination termed "scorpion" and described in Whitcombe et al., (1999) Detection of PCR products using self-probing amplicons and fluorescence, Nature Biotech. 17:804-807. The scorpion primer designed according to the present invention incorporates the typical elements of the scorpion, namely a probe portion, a stem loop portion and a primer portion. Further, in a scorpion designed according to the present invention, the primer portion contains the internally placed selective nucleotide. Optionally, the primer portion in a scorpion designed according to the present invention may contain one or more chemically modified nucleotides.

In summary, the allele-specific primer of the present invention possesses at a minimum the following four characteristics: 1) a 5'-portion, at least partially complementary to both desired and undesired variants of the target sequence; 2) an internal selective nucleotide, complementary only to the desired variant of the target sequence and situated within the 3'-portion; 3) a 3'-portion, at least partially complementary to both desired and undesired variants of the target sequence; and 4) the 3'-terminal nucleotide complementary to both desired and undesired versions of the target sequence. The 5'-portion and the 3'-portion may contain additional selective nucleotides that are complementary only to the desired version of the target sequence, as long as the 3'-terminal nucleotide of the primer is complementary to both desired and undesired version of the target sequence.

Empirical selection of a suitable 5'-portion and 3'-portion of the allele-specific primer can be carried out routinely by one of skill in the art. Specifically, the length, degree of complementarity of the 5'-portion and the 3'-portion and chemical modifications of nucleotides in the 5'-portion and the 3'-portion of the primer can be varied, as long as the primer possesses the four characteristics set forth above. Preferably, suitability of a particular allele-specific primer is determined empirically by using the primer in an allele-specific amplification. The suitability of the primer is indicated by the selectivity of the amplification utilizing the primer.

In another aspect, the present invention is a method of allele-specific amplification of a target nucleic acid. The amplification involves the use of an allele-specific primer having a selective nucleotide, placed internally of the 3'-end of the primer, between a and b, preferably c nucleotides internally of the 3'-end.

In one embodiment, the present invention is a method of allele-specific amplification of a variant of a target sequence, which exists in the form of several variant sequences, the method comprising: providing a sample, possibly containing at least one variant of a target sequence; providing a first oligonucleotide, at least partially complementary to one or more variants of the target sequence; providing a second oligonucleotide, at least partially complementary to one or more variants of the target sequence, but having at least one internal selective nucleotide complementary to only one variant of the target sequence; providing conditions suitable for the hybridization of said first and second oligonucleotides to at least one variant of the target sequence; providing conditions suitable for the oligonucleotide extension by a nucleic acid polymerase; wherein said polymerase is capable of extending said second oligonucleotide when it is hybridized to the variant of the target sequence for which it has said complementary internal selective nucleotide, and substantially less when said second oligonucleotide is hybridized to the variant of the target sequence for which it has a non-complementary internal selective nucleotide; and repeating the sequence of hybridization and extension steps multiple times.

In some embodiments of the invention, the amplification involves the polymerase chain reaction, i.e. repeated cycles of template denaturation, annealing (hybridization) of the oligonucleotide primer to the template, and extension of the primer by the nucleic acid polymerase. In some embodiments, annealing and extension occur at the same temperature step.

In some embodiments, the amplification reaction involves a hot start protocol. In the context of allele-specific amplification, the selectivity of the allele-specific primers with respect to the mismatched target may be enhanced by the use of a hot start protocol. Many hot start protocols are known in the art, for example, the use of wax, separating the critical reagents from the rest of the reaction mixture (U.S. Pat. No. 5,411,876), the use of a nucleic acid polymerase, reversibly inactivated by an antibody (U.S. Pat. No. 5,338,671), a nucleic acid polymerase reversibly inactivated by an oligonucleotide that is designed to specifically bind its active site (U.S. Pat. No. 5,840,867) or the use of a nucleic acid polymerase with reversible chemical modifications, as described e.g. in U.S. Pat. Nos. 5,677,152 and 5,773,528.

In some embodiments of the invention, the allele-specific amplification assay is real-time PCR assay. In a real-time PCR assay, the measure of amplification is the "threshold cycle" or Ct value. In the context of the allele-specific real-time PCR assay, the difference in Ct values between the matched and the mismatched templates is a measure of discrimination between the alleles or the selectivity of the assay. A greater difference indicates a greater delay in amplification of the mismatched template and thus a greater discrimination between alleles. Often the mismatched template is present in much greater amounts than the matched template. For example, in tissue samples, only a small fraction of cells may be malignant and carry the mutation targeted by the allele-specific amplification assay ("matched template"). The mismatched template present in normal cells may be amplified less efficiently, but the overwhelming numbers of normal cells will overcome any delay in amplification and erase any advantage of the mutant template. To detect rare mutations in the presence of the wild-type template, the specificity of the allele-specific amplification assay is critical.

The allele-specific amplification assay of the present invention may employ any suitable nucleic acid polymerase known in the art. For an allele-specific PCR assay of the present invention, any thermostable nucleic acid polymerase may be used. A modified, engineered or chimeric polymerase may also be used. It is sometimes desirable to use an enzyme without the proofreading (3'-5'-exonuclease) activity, such as for example, Taq DNA polymerase. It may also be desirable to use enzymes, substantially or entirely lacking the 5'-3' nuclease activity, such as described in U.S. Pat. No. 5,795,762. One example of such an enzyme is ΔZ05 polymerase. It may sometimes be desirable to have an enzyme with a "hot start" capability, such as the reversibly modified enzymes described in U.S. Pat. Nos. 5,677,152 and 5,773,528. One example of a hot-start enzyme is ΔZ05-Gold polymerase. It is generally known that the specificity of an allele-specific primer may vary somewhat among different enzymes. See Newton et al. (1989) Analysis of any point mutation in DNA. The amplification refractory mutation system (ARMS). Nucl. Acids Res. 17:2503-2516. Based on the protocols described in Newton (supra) a person of ordinary skill would be able to optimize the reaction parameters, for example, by changing the salt concentration and temperature profile in order to achieve maximum specificity with each enzyme and select the best enzyme for a particular assay.

A special advantage of the allele-specific PCR of the present invention is the ability to use polymerases with proofreading 3'-5'-nuclease activity. These enzymes typically have higher fidelity (i.e. fewer misincorporated nucleotides in the final product) than the enzymes without the proofreading activity. For example, error rate for Taq DNA polymerase (which does not have a proofreading function) is about $10^{-4}$. Tindall et al. (1988) Fidelity of DNA synthesis by the *Thermus aquaticus* DNA polymerase. Biochemistry, 27:6008-6013. By comparison, the error rate of a proofreading thermostable Pfu DNA polymerase is about $10^{-6}$. Andre et al. (1997) Fidelity and mutational spectrum of Pfu DNA polymerase on a human mitochondrial DNA sequence, Genome Res. 7:843-852. Prior to the present invention, a high-fidelity proofreading polymerase could not be used with allele-specific PCR. See U.S. Pat. No. 5,639,611. The nuclease activity of the enzyme would remove the mismatched selective nucleotide from the 3'-terminus of the primer thus eliminating allele-specificity of the primer. In the present invention, the allele-specific primer has a selective nucleotide not at the 3'-end but internally. The internal mismatch is an inefficient substrate for the exonuclease activity of a proofreading enzyme. It has been observed that the ability of the exonuclease to remove mismatched nucleotides drops dramatically went the mismatch is located away from the 3'-end. Fidalgo-Da Silva et al. (2007) DNA polymerase proofreading: active site switching catalyzed by the bacteriophage T4 DNA polymerase, Nucl. Acids Res. 35:5452-5463. The rate of removal of three nucleotides is much lower than two nucleotides. Reddy et al. (1992) Processive proofreading is intrinsic to T4 DNA polymerase. J. Biol. Chem. 267:14157-14166. Therefore the primer with an internal selective nucleotide of the present invention may be used with a proofreading nucleotide polymerase. A person of skill in the art would recognize how to optimize reaction conditions, for example by changing the composition of the reaction buffer and concentration of nucleic acid precursors in order to minimize exonuclease activity of the enzyme without compromising allele-specific amplification. See e.g. Goodman et. al. (1993) Biochemical basis of DNA replication fidelity, Crit. Rev. Biochem. Mol. Biol. 28:83-126 for conditions favoring polymerization and conditions favoring nuclease digestion activities of various nucleic acid polymerases.

In some embodiments of the method, the amplification products may be detected by any technique known in the art, including but not limited to the use of labeled primers and probes as well as various nucleic acid-binding dyes. The means of detection may be specific to one variant of the target sequence, or may be generic to all variants of the target sequence or even to all double-stranded DNA.

The amplification products may be detected after the amplification has been completed, for example, by gel electrophoresis of unlabeled products and staining of the gel with a nucleic acid-binding dye. Alternatively, the amplification products may carry a radioactive or a chemical label, either by virtue of incorporation during synthesis or by virtue of being the extension products of a labeled primer. After, or during electrophoresis, the labeled amplification products may be detected with suitable radiological or chemical tools known in the art. After electrophoresis, the products may also be detected with a target-specific probe labeled by any one of the methods known in the art. The labeled probe may also be applied to the target without electrophoresis, i.e. in a "dot blot" assay or the like.

In other embodiments, the presence of the amplification product may be detected in a homogeneous assay, i.e. an assay where the nascent product is detected during the cycles of amplification, or at least in the same unopened tube, and no post-amplification handling is required. A homogeneous amplification assay has been described for example, in U.S. Pat. No. 5,210,015. Homogeneous amplification assay using nucleic acid-intercalating dyes has been described for example, in U.S. Pat. Nos. 5,871,908 and 6,569,627. The homogeneous assay may also employ fluorescent probes labeled with two interacting fluorophores, such as "molecular beacon" probes (Tyagi et al., (1996) Nat. Biotechnol., 14:303-308) or fluorescently labeled nuclease probes (Livak et al., (1995) PCR Meth. Appl., 4:357-362). The amplification products may also be detected using a unimolecular primer-probe combination termed "scorpion." Whitcombe et al., (1999) Detection of PCR products using self-probing amplicons and fluorescence, Nature Biotech. 17:804-807. The primer portion of the scorpion oligonucleotide may be an allele-specific primer designed according to the present invention.

In certain variations of the method of the present invention, the amplification product may also be identified by virtue of its distinctive melting temperature, see U.S. Pat. Nos. 5,871, 908 and 6,569,627.

In another embodiment, the invention provides a reaction mixture for selectively amplifying the desired variant of the target sequence, the target sequence existing in the form of several variant sequences, the mixture comprising a first oligonucleotide, at least partially complementary to one or more variants of the target sequence; and a second oligonucleotide, at least partially complementary to one or more variants of the target sequence, but having at least one internal selective nucleotide complementary to only one variant of the target sequence. The reaction mixture may also contain a nucleic acid polymerase which is capable of extending said second oligonucleotide when it is hybridized to the variant of the target sequence for which it has said complementary internal selective nucleotide, and substantially less when said second oligonucleotide is hybridized to the variant of the target sequence for which it has a non-complementary internal selective nucleotide. In some embodiments, the reaction mixture further comprises the reagents and solutions generally necessary for the amplification of nucleic acids, including nucleic acid precursors, i.e. nucleoside triphosphates, and organic and inorganic ions, suitable for the support of the activity of the nucleotide polymerase.

In another embodiment, the invention provides kits for conducting allele-specific amplification according to the invention. The kit generally includes assay-specific components as well as components generally required for performing nucleic acid amplification. As the assay-specific components, the allele-specific amplification kit of the present invention contains a first oligonucleotide, at least partially complementary to one or more variants of the target sequence; a second oligonucleotide, at least partially complementary to one or more variants of the target sequence, but having at least one internal selective nucleotide complementary to only one variant of the target sequence; and optionally, a control nucleic acid sequence comprising an amount of at least one variant of the target sequence, at least partially complementary to the oligonucleotides enclosed in the kit. In some embodiments, more than one variant of the control nucleic acid sequence may be enclosed. As the components generally required for nucleic acid amplification, the kit of the present invention may include one or more of a nucleic acid polymerase, nucleic acid precursors, such as nucleoside triphosphates deoxy-ribonucleoside triphosphates or ribonucleoside triphosphates, a pyrophosphatase, for minimizing pyrophosphorolysis of nucleic acids, a uracil N-glycosylase (UNG) for protection against carry-over contamination of amplification reactions, pre-made reagents and buffers necessary for the amplification reaction and detection, and a set of instructions for conducting allele-specific amplification according to the present invention.

The following examples and figures are provided to aid the understanding of the present invention, the true scope of which is set forth in the appended claims. It is understood that modifications can be made in the procedures set forth without departing from the spirit of the invention.

EXAMPLES

In the examples below, two variants of the template sequence were used: a matched variant, with a sequence complementary to the selective nucleotide in the allele-specific primer and a mismatched variant, with a sequence non-complementary to the selective nucleotide in the allele-specific primer.

As a matched target, the examples utilized the V600E mutation of the human BRAF gene (GeneBank reference). The matched variant was a plasmid DNA with the insert incorporating the BRAF V600E mutant sequence (SEQ ID NO: 19), while the mismatched variant was the same plasmid with the BRAF wild-type sequence (SEQ ID NO: 20).

(BRAF V600E mutant sequence fragment)
SED ID NO: 19
5'-AGTAAAAATAGGTGATTTTGGTCTAGCTACAGAGAAATCTCGATGG

AGTGGGTCCCATCAGTTTGAACAGTTGTCTGGATCCATTTTGTGGATGG

TAAGAATTGAGGCTA-3'

(BRAF wild-type sequence fragment)
SEQ ID NO: 20
5'-AGTAAAAATAGGTGATTTTGGTCTAGCTACAGTGAAATCTCGATGG

AGTGGGTCCCATCAGTTTGAACAGYMTCTGGATCCATTTTGTGGATGGT

AAGAATTGAGGCTA-3'

This mutation is a valine-to-glutamate change of amino acid 600, that results from a thymine (T) to adenine (A) transition at nucleotide 1799 of the BRAF gene. The mutation is found in many cancers and is thought to contribute to cancer progression, as it results in constitutive activation of the MAPK pathway. Detection of this single nucleotide change in a population of tumor cells has utility in the diagnosis and treatment of human cancers.

The mutant target is "matched", i.e. forms an A-T Watson-Crick pair with the selective nucleotide of each of the allele-specific primers (Table A). The mismatched target is the wild-type BRAF sequence. The mismatched target forms a mismatch with the selective nucleotide of each of the allele-specific primers.

TABLE A

| Primers | | |
|---|---|---|
| Seq ID | Function | Sequence |
| 1 | Forward primer | 5'-TAAAAATAGGTGATTTTGGTCTAGCTA CAGAGA-3'* |
| 2 | Forward primer | 5'-TAAAAATAGGTGATTTTGGTCTAGCTA CYGAGA-3' |
| 3 | Forward primer | 5'-TAAAAATAGGTGATTTTGGTCTAGCTA CAGYGA-3' |
| 4 | Forward primer | 5'-TAAAAATAGGTGATTTTGGTCTAGCTA CAGAGX-3' |
| 5 | Forward primer | 5'-TAAAAATAGGTGATTTTGGTCTAGCTA CYGAGY-3' |
| 6 | Forward primer | 5'-GTAAAAATAGGTGATTTTGGTCTAGCT ACAGAG-3' |
| 7 | Forward primer | 5'-GTAAAAATAGGTGATTTTGGTCTAGCT ACAGYG-3' |
| 8 | Forward primer | 5'-GTAAAAATAGGTGATTTTGGTCTAGCT ACYGAG-3' |
| 9 | Forward primer | 5'-GTAAAAATAGGTGATTTTGGTCTAGCT ACYGYG-3' |

TABLE A -continued

Primers

| Seq ID | Function | Sequence |
|---|---|---|
| 10 | Forward primer | 5'-GTAAAAATAGGTGATMGGTCTAGCTA ZAG<u>Y</u>G-3' |
| 11 | Reverse primer | 5'-TAGCCTCAATTCTTACCATCCACA<u>X</u>-3' |

*selective nucleotide is underlined
X-N$^6$-benzyl-dA
Y-N$^6$-para-tert-butyl-benzyl-dA
Z-N$^6$-para-tert-butyl-benzyl-dC

Example 1

Allele-Specific Amplification Using a Primer with an Internal Selective Nucleotide In this example, two variants of the template sequence were used: a matched variant, with a sequence complementary to the selective nucleotide in the allele-specific primer and a mismatched variant, with a sequence non-complementary to the selective nucleotide in the allele-specific primer. The matched variant was a plasmid DNA with the insert representing the BRAF sequence with a V600E mutation. The mismatched variant was the same plasmid with the BRAF wild-type sequence. The forward primers (SEQ ID NO: 1-4) and reverse primer (SEQ ID NO: 11) are shown in Table A. The forward allele-specific primers were designed with the selective nucleotide internal of the 3' terminus, at the N-2 position. Some primers contained chemical modifications where indicated.

Each 50 μL reaction contained 10$^5$ copies of either target, 8% glycerol, 50 mM tricine (pH 7.7), 45 mM potassium acetate (pH 7.5), 200 μM each dATP, dCTP and dGTP, 400 μM dUTP, 0.1 μM forward primer, 0.7 μM reverse primer, 2 μM Syto-13 intercalating dye, 1% DMSO, 2 units of uracil-N-glycosylase (UNG), 50 units of ΔZ05-Gold DNA polymerase, and 3 mM mangnesium acetate. Amplification and analysis were done using the Roche LightCycler 480 instrument. The reactions were subjected to the following temperature profile: 50° C. for 5 minutes (UNG step), 95° C. for 10 minutes, followed by 60-70 cycles of 95° C. for 15 seconds and 59° C. for 40 seconds. Fluorescence data was collected at 495-525 nm at the end of each 59° C. step.

The results are shown on FIG. 1 and Table 1. The selectivity of the amplification is measured by the difference in the $C_t$ value ($\Delta C_t$) between the matched and the mismatched targets. $\Delta C_t$ for each experiment is indicated on each diagram. The data shows that the matched (mutant) variant of the target was amplified selectively over the mismatched (wild-type) variant. The selectivity was enhanced by chemical modification of the nucleotides in the primers. In this table, position N denotes the nucleotide at the 3' end.

TABLE 1

| Forward primer | Position of the selective nucleotide | Chemical modification | Average $C_t$ wild-type target | Average $C_t$ mutant target | $\Delta C_t$ |
|---|---|---|---|---|---|
| SEQ ID NO: 1 | N-2 | none | 33.7 | 29.4 | 4.3 |
| SEQ ID NO. 2 | N-2 | Y* at N-4 | 44.0 | 31.9 | 12.1 |
| SEQ ID NO. 3 | N-2 | Y at N-2 | 42.1 | 32.1 | 10.0 |
| SEQ ID NO. 4 | N-2 | X at 3' end | 49.0 | 33.3 | 15.7 |

*Y - N$^6$-para-tert-butyl-benzyl-dA
X - N$^6$-benzyl-dA

Example 2

Allele-Specific Amplification Using Primers with an Internal Selective Nucleotide and Different Nucleic Acid Polymerases In this example, the same matched (mutant) and mismatched (wild-type) targets as in Example 1 were amplified using primers shown in Table A. Amplification was carried out in the presence of Z05, ΔZ05, or ΔZ05-Gold polymerase.

All reactions were done in triplicate, in 15 μL volumes containing 10$^5$ copies of either target, 200 μM each dATP, dCTP and dGTP, 400 μM dUTP, 0.1 μM forward primer, 0.7 μM reverse primer, 2 μM Syto-13 intercalating dye, 1% DMSO, 0.04 U/μl uracil-N-glycosylase (UNG), and 3 mM magnesium acetate. Z05 reactions contained 3 U of polymerase, 130 mM potassium acetate (pH 7.5), 5% glycerol, and 50 mM Tricine (pH 8.3). ΔZ05 reactions contained 3 U of polymerase, 25 mM potassium acetate (pH 7.5), 5% glycerol, and 50 mM Tricine (pH 8.3). Δ05-Gold reactions contained 15 U of polymerase, 45 mM potassium acetate (pH 7.5), 8% glycerol, and 50 mM Tricine (pH 7.7).

Amplification and analysis were done using the Roche LightCycler 480 instrument. The reactions were subjected to the following temperature profile: 50° C. for 5 minutes (UNG step), 95° C. for 10 minutes, followed by 99 cycles of 95° C. for 15 seconds and 59° C. for 40 seconds. Fluorescence data was collected at 465-510 nm at the end of each 59° C. step.

The results are shown in Table 2. The selectivity of amplification is measured by the difference in the $C_t$ value ($\Delta C_t$) between the matched and the mismatched targets. $\Delta C_t$ for each experiment is indicated in Table 2. The data shows that the matched (mutant) variant of the target was amplified selectively over the mismatched (wild-type) variant. The selectivity was enhanced by the alkyl modification of the nucleotides in the primers. In this table, position N denotes the nucleotide at the 3' end.

TABLE 2

| SEQ ID | SELECTIVE NUCLEOTIDE POSITION | Z05 | | | DZ05 | | | ΔZ05-GOLD | | |
|---|---|---|---|---|---|---|---|---|---|---|
| | | Mut Ct$_{avg}$ | Wt Ct$_{avg}$ | $\Delta Ct_{(wt-mut)}$ | Mut Ct$_{avg}$ | Wt Ct$_{avg}$ | $\Delta Ct_{(wt-mut)}$ | Mut Ct$_{avg}$ | Wt Ct$_{avg}$ | $\Delta Ct_{(wt-mut)}$ |
| 1 | N-2 | 24.1 | 24.9 | 0.8 | 25.9 | 27.3 | 1.4 | 29.8 | 34.0 | 4.2 |
| 3 | N-2 | 25.1 | 29.6 | 4.5 | 27.2 | 38.4 | 11.2 | 35.1 | 51.5 | 16.4 |
| 5 | N-2 | 29.0 | 47.0 | 18.0 | N/A | N/A | N/A | 94.0 | 100.0 | 6.0 |
| 6 | N-1 | 25.0 | 27.0 | 2.0 | 25.2 | 32.1 | 6.9 | 28.9 | 42.0 | 13.2 |

TABLE 2-continued

| SEQ ID | SELECTIVE NUCLEOTIDE POSITION | Z05 | | | DZ05 | | | ΔZ05-GOLD | | |
|---|---|---|---|---|---|---|---|---|---|---|
| | | Mut Ct$_{avg}$ | Wt Ct$_{avg}$ | ΔCt$_{(wt-mut)}$ | Mut Ct$_{avg}$ | Wt Ct$_{avg}$ | ΔCt$_{(wt-mut)}$ | Mut Ct$_{avg}$ | Wt Ct$_{avg}$ | ΔCt$_{(wt-mut)}$ |
| 7 | N-1 | 24.2 | 30.5 | 6.3 | 26.3 | 38.8 | 12.5 | 31.7 | 60.0 | 28.2 |
| 8 | N-1 | 24.3 | 31.0 | 6.8 | 26.4 | 39.0 | 12.6 | 31.3 | 55.7 | 24.4 |
| 9 | N-1 | 25.3 | 39.9 | 14.5 | 48.4 | 100.0 | 51.6 | 56.2 | 92.6 | 36.4 |
| 10 | N-1 | 24.3 | 36.8 | 12.6 | 38.5 | 77.3 | 38.7 | 56.7 | 89.3 | 32.6 |

N/A—no data

Example 3

Allele-Specific Amplification Using Scorpion ARMS-Like Primers with Internal Base Modifications and/or Internal Selective Nucleotide

TABLE 3

| SEQ ID | FUNCTION | PRIMER SEQUENCE |
|---|---|---|
| 12 | FORWARD PRIMER | AGTAAAAATAGGTGATTTTGGTCTAGCTACAGA |
| 13 | FORWARD PRIMER, PROBE | FCCCGCGCGGACCCACTCCATCGAGAGCGCGGG QJAGTAAAAATAGGTGATTTTGGTCTAGCTACACA |
| 14 | FORWARD PRIMER | AGTAAAAATAGGTGATTTTGGTCTAGCTACYGA |
| 15 | FORWARD PRIMER, PROBE | FCCCGCGCGGACCCACTCCATCGAGAGCGCGGG QJAGTAAAAATAGGTGATTTTGGTCTAGCTACYGA |
| 6 | FORWARD PRIMER | GTAAAAATAGGTGATTTTGGTCTAGCTACAGAG |
| 16 | FORWARD PRIMER, PROBE | FCCCGCGCGGACCCACTCCATCGAGAGCGCGGG QJGTAAAAATAGGTGATTTTGGTCTAGCTACAGAG |
| 9 | FORWARD PRIMER | GTAAAAATAGGTGATTTTGGTCTAGCTACYGYG |
| 17 | FORWARD PRIMER, PROBE | FCCCGCGCGGACCCACTCCATCGAGAGCGCGGGQ JGTAAAAATAGGTGATTTTGGTCTAGCTACYGYG |
| 11 | REVERSE PRIMERS | TAGCCTCAATTCTTACCATCCACAX |
| 18 | PROBE | FTCTCGATGGAGTGGGTCCQp |

X-N⁶-benzyl-dA
Y-N⁶-para-tert-butyl-benzyl-dA
F-cx-FAM donor fluorophore
Q-BHQ-2 "Black Hole" quencher
J-HEG
p-3'-phosphate
*The allele selective nucleotide is underlined (N or N-1 position from 3' terminus)

In this example, two variants of the template sequence were present in equal amounts, a matched variant, complementary to the primer sequence and a mismatched variant. The matched variant was a plasmid DNA with the insert representing the BRAF V600E mutant sequence (SEQ ID NO: 1), while the mismatched variant was the same plasmid with the BRAF wild-type sequence (SEQ ID NO: 2). The forward primers (SEQ ID NO: 6, 9, 12-17) and reverse primer (SEQ ID NO: 11) are as described in Table 3. The forward, ASPCR primers, were designed with the SNP at, or near the 3' terminal position, either with or without N6-tert-butyl-benzyl-dA modification(s). The ASPCR primer is paired with a downstream detection probe (SEQ ID: 18) or linked to the probe complement in a closed Scorpion ARMS-like format.

Each 50 uL reaction contained $10^5$ copies of either target, 5% glycerol, 50 mM tricine (pH 8.3), 150 mM potassium acetate (pH 7.5), 200 μM each of dATP, dCTP and dGTP, 400 μM dUTP, 0.4 μM forward primer, 0.4 μM reverse primer, 1% DMSO, 2 units uracil-N-glycosylase (UNG), 10 units Z05 polymerase, and 3 mM magnesium acetate. 0.2 uM of detection probe was added to reactions containing Primers 6, 9, 12 and 14 where the probe complement is not linked to the forward primer.

Amplification and analysis were done using the Roche LightCycler 480 instrument. The reactions were subjected to the following temperature profile: 50° C. for 5 minutes (UNG step) followed by 95 cycles of 95° C. for 15 seconds and 59° C. for 40 seconds. Fluorescence data was collected at the 495-525 nm range at the end of each 59° C. anneal/extend step.

Figures 1, 2:
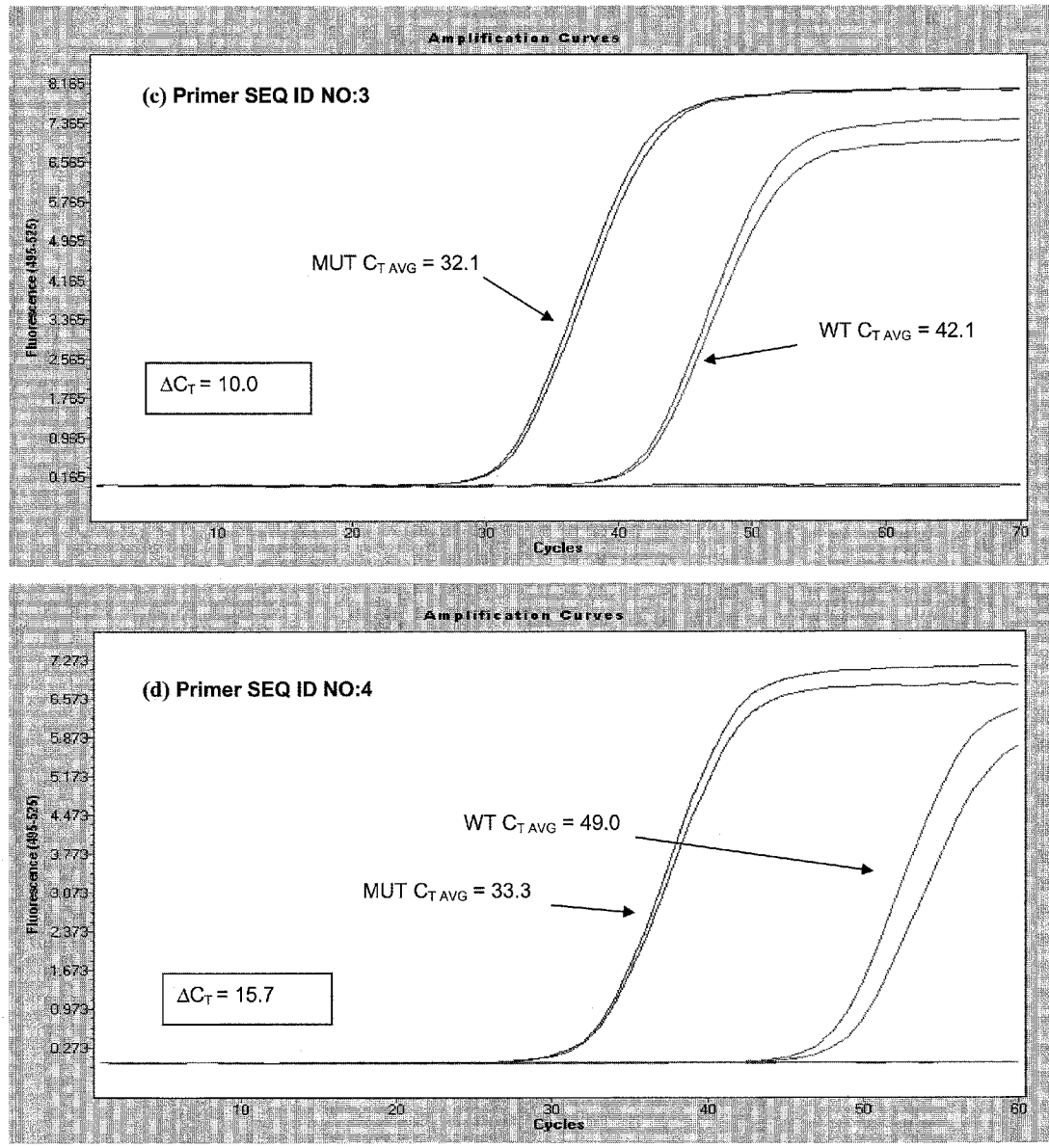
FIG. 2 shows the results of allele-specific amplification using various nucleic acid polymerases and various primers with 3' selective nucleotide as a control.
Figure 2:
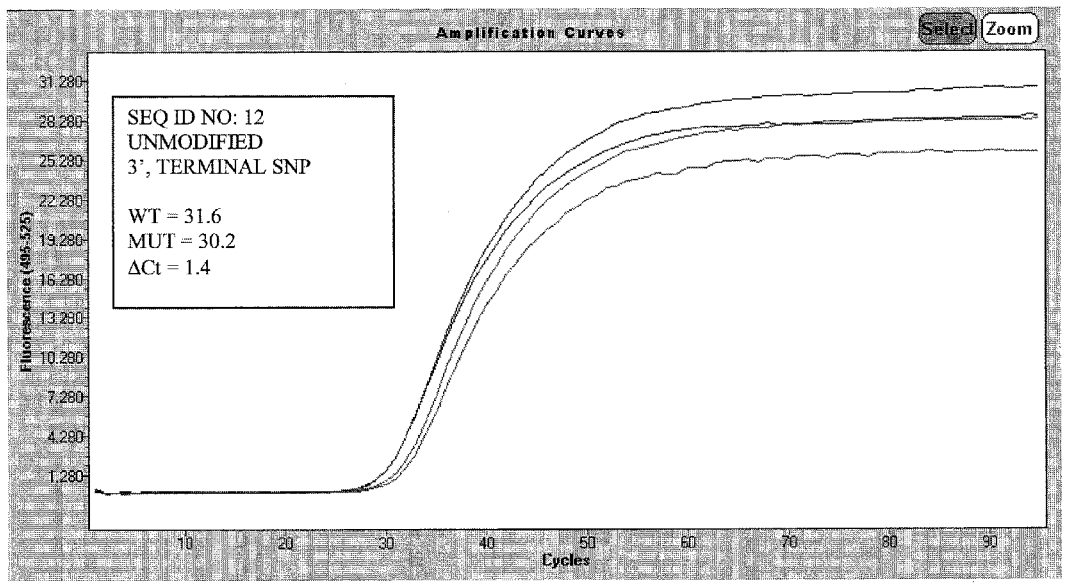
Figure 1:
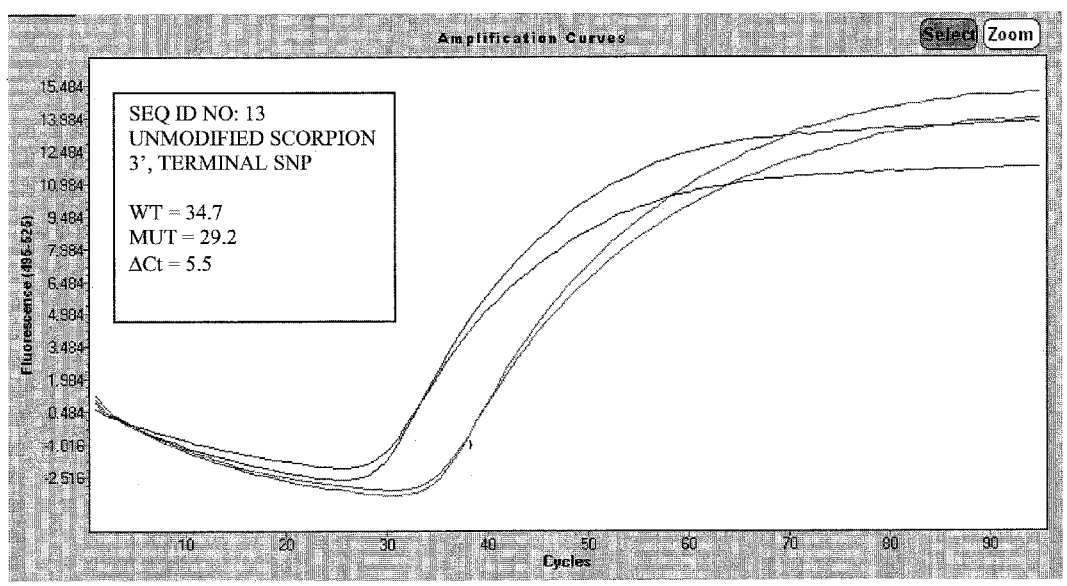
Figure 2:
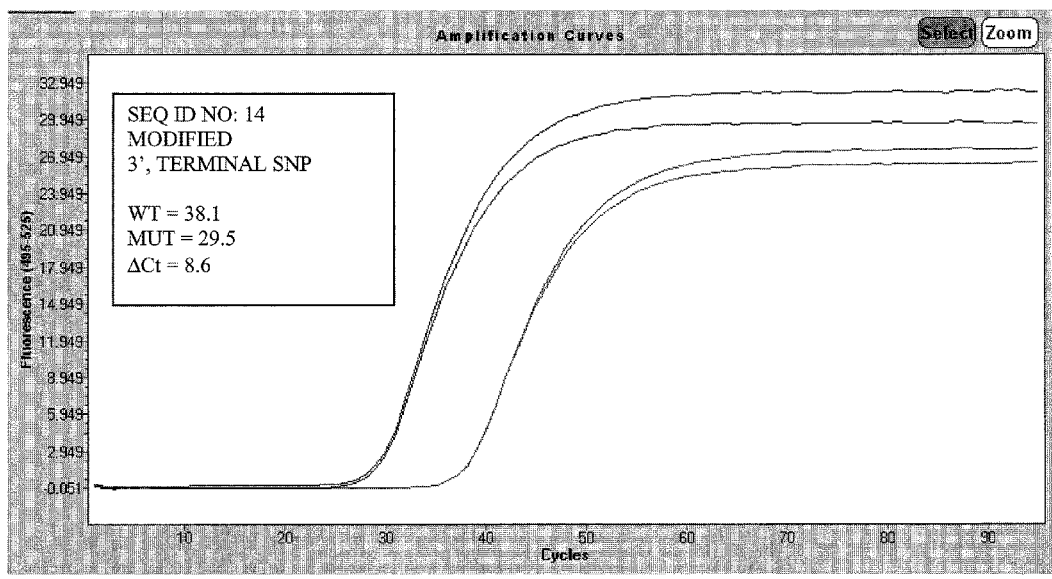
Figure 2:
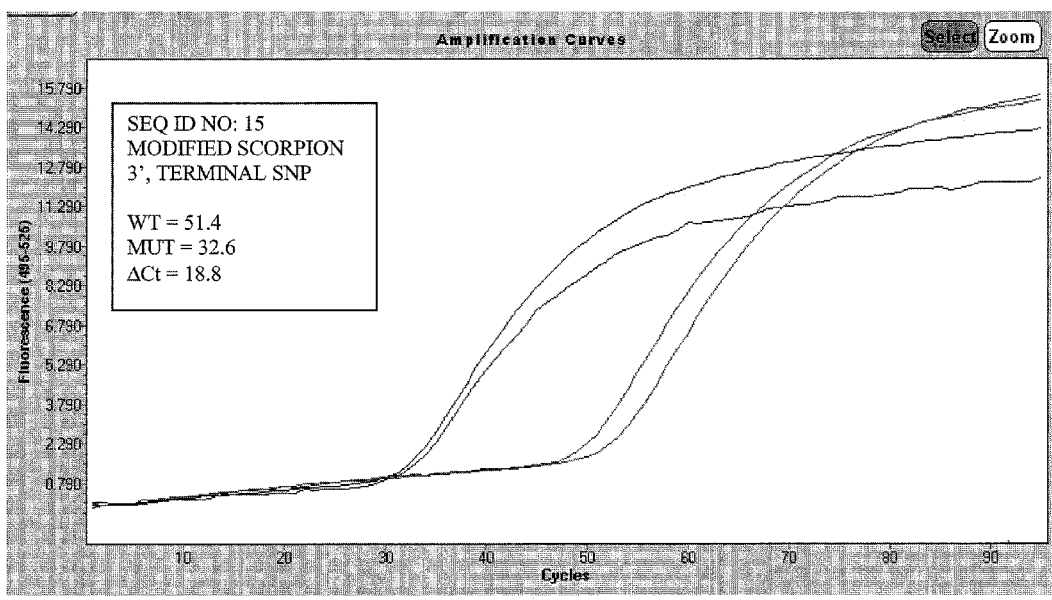
Figures 1, 3:
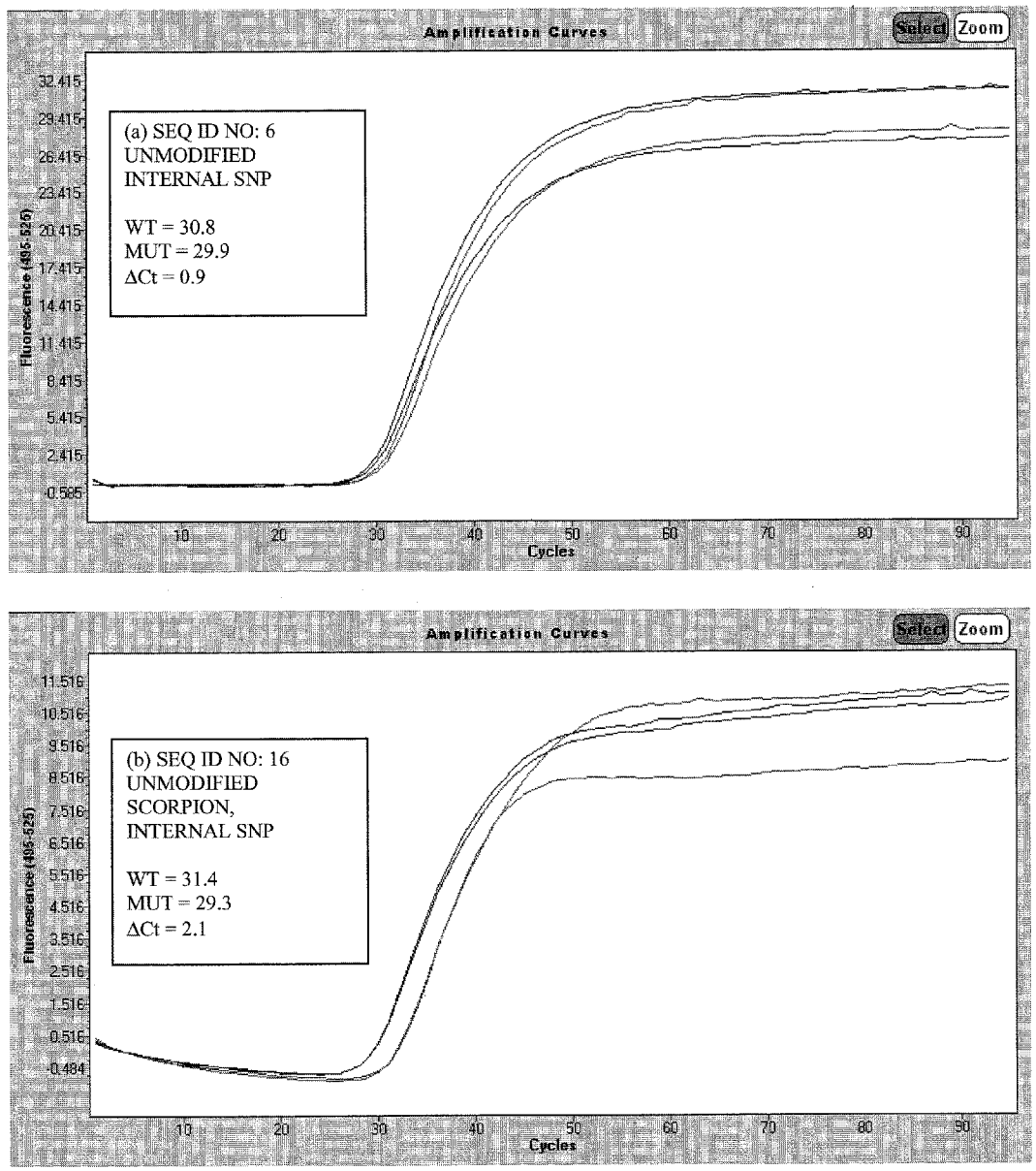
FIG. 3 shows the results of allele-specific amplification using various nucleic acid polymerases and various primers with internal selective nucleotide according to the present invention, including primers having a scorpion ARMS format.
Figure 3:
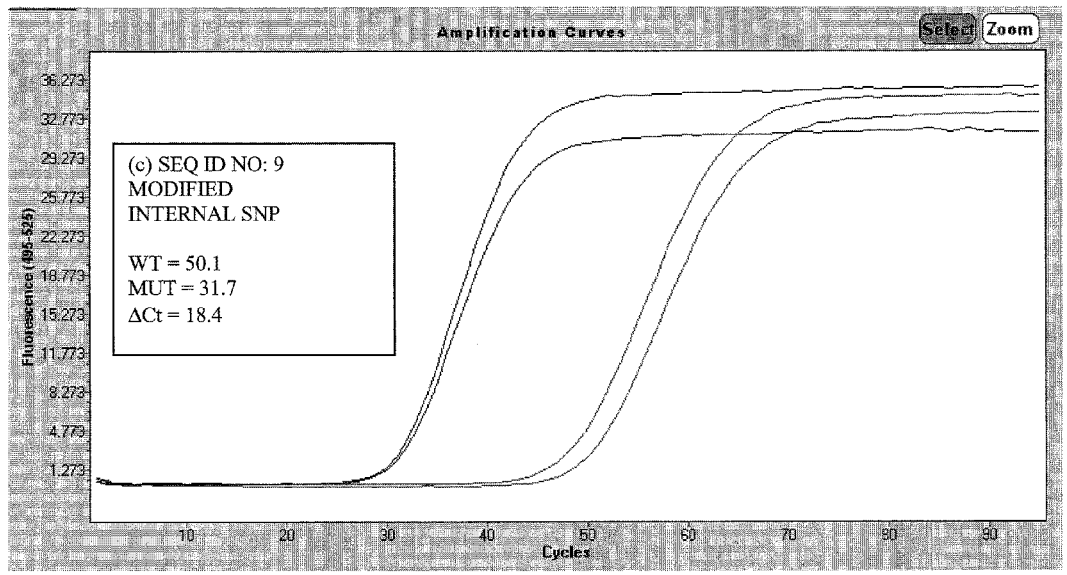
Figure 2:
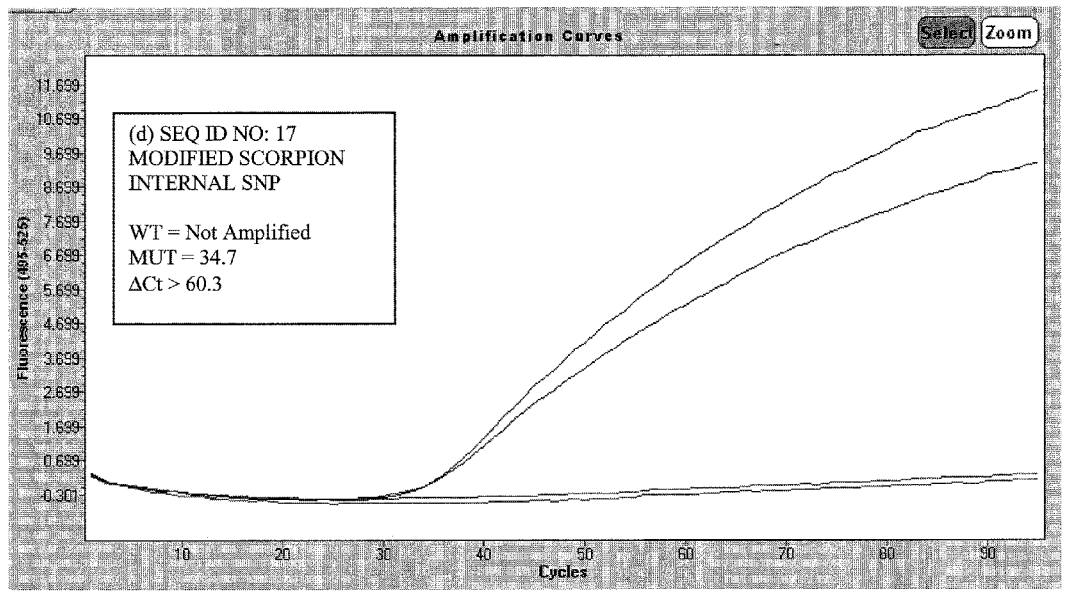

The results are shown on FIG. 2 and Table 4. The selectivity of the amplification is measured by the difference in the Ct value (ΔCt) between the matched and the mismatched targets. ΔCt for each experiment is indicated on each diagram and summarized in Table 4. The data shows that the matched (mutant) variant of the target was amplified selectively over the mismatched (wild-type) variant using either the individual primer and probe or the primer and probe linked in a closed Scorpion ARMS-like format. Discrimination was achieved whether the selective nucleotide was at the 3' terminus or internal. Additionally, the selectivity of amplification was enhanced by addition of one or more alkyl modifications.

TABLE 4

| SEQ ID | PRIMER SEQUENCE | POSITION OF SELECTIVE NUCLEOTIDE | PRIMER FORMAT | MODIFICATION OF PRIMING SEGMENT | WT CT$_{AVG}$ | MUT CT$_{AVG}$ | ΔCT |
|---|---|---|---|---|---|---|---|
| 12 | AGTAAAAATAGGTGATTTTGGTCTAGCTACAGA | 3' terminus | Traditional | none | 31.6 | 30.2 | 1.4 |

TABLE 4 -continued

| SEQ ID | PRIMER SEQUENCE | POSITION OF SELECTIVE NUCLEOTIDE | PRIMER FORMAT | MODIFICATION OF PRIMING SEGMENT | WT $CT_{AVG}$ | MUT $CT_{AVG}$ | ΔCT |
|---|---|---|---|---|---|---|---|
| 13 | FCCCGCGCGGACCCACTCCATCG AGAGCGCGGGQJAGTAAAAATAG GTGATTTTGGTCTAGCTACAGA | 3' terminus | Scorpion ARMS | none | 34.7 | 29.2 | 5.5 |
| 14 | AGTAAAAATAGGTGATTTTGGTC TAGCTACYGA | 3' terminus | Traditional | Y at N-2 | 38.1 | 29.5 | 8.6 |
| 15 | FCCCGCGCGGACCCACTCCATCG AGAGCGCGGGQJAGTAAAAATAG GTGATTTTGGTCTAGCTACYGA | 3' terminus | Scorpion ARMS | Y at N-2 | 51.4 | 32.6 | 18.8 |
| 6 | GTAAAAATAGGTGATTTTGGTCT AGCTACAGAG | 3' penultimate | Traditional | none | 30.8 | 29.9 | 0.9 |
| 16 | FCCCGCGCGGACCCACTCCATCG AGAGCGCGGGQJGTAAAAATAGG TGATTTTGGTCTAGCTACAGAG | 3' penultimate | Scorpion ARMS | none | 31.4 | 29.3 | 2.1 |
| 9 | GTAAAAATAGGTGATTTTFGGTC TAGCTACYGYG | 3' penultimate | Traditional | Y at N-1 and N-3 | 50.1 | 31.7 | 18.4 |
| 17 | FCCCGCGCGGACCCACTCCATCG AGAGCGCGGGQJGTAAAAATAGG TGATTTTGGTCTAGCTACYGYG | 3' penultimate | Scorpion ARMS | Y at N-1 and N-3 | Not Amplified | 34.7 | >60.3 |

While the invention has been described in detail with reference to specific examples, it will be apparent to one skilled in the art that various modifications can be made within the scope of this invention. Thus the scope of the invention should not be limited by any of the examples described herein, but by the claims presented below.

All publications including patent applications and patents cited in this application are incorporated by reference in their entirety for all purposes to the same extent as if each individual publications were individually indicated to be incorporated by reference for all purposes.

---

The invention claimed is:

1. A method of allele-specific amplification by polymerase chain reaction (PCR) and detection of a desired variant of a target nucleic acid, the target nucleic acid existing in the form of several variant sequences, the method comprising:
   (a) providing a reaction mixture in liquid solution that comprises a first oligonucleotide at least partially complementary to one or more variants of the target nucleic acid, and a second oligonucleotide at least partially complementary to one or more variants of the target nucleic acid and has at least one selective nucleotide that is complementary to a corresponding nucleotide in the desired variant of the target nucleic acid but not complementary to the corresponding nucleotide in undesired variants of the target nucleic acid, wherein said selective nucleotide is placed internally of the 3' terminus, and wherein said second oligonucleotide further comprises at least one nucleotide with a base covalently modified at the exocyclic amino group;
   (b) hybridizing said first and second oligonucleotides to at least one variant of the target nucleic acid;
   (c) providing conditions for the extension of said first and second oligonucleotides to at least one variant of the target nucleic acid by a nucleic acid polymerase, wherein said polymerase is capable of extending said second oligonucleotide preferentially when said selective nucleotide forms a base pair with the desired variant of the target nucleic acid, and substantially less when said selective nucleotide does not form a base pair with the desired variant of the target nucleic acid; and
   (d) detecting the product of primer extension in step (c);
   wherein said method of amplification and detection are performed in a homogeneous assay.

2. The method of claim 1, wherein said nucleic acid polymerase in step (c) is capable of extending said second oligonucleotide exclusively when said selective nucleotide forms a base pair with the desired variant of the target nucleic acid.

3. The method of claim 1, wherein said selective nucleotide is at the position between 1 and 5 nucleotides near the 3'-terminus of the oligonucleotide.

4. The method of claim 1, wherein said nucleic acid polymerase is selected from the group consisting of Taq DNA polymerase, Z05 DNA polymerase, ΔZ05 DNA polymerase and ΔZ05-Gold DNA polymerase.

5. The method of claim 1 wherein said nucleic acid polymerase possesses 3'-5' nuclease activity.

6. The method of claim 5, wherein said nucleic acid polymerase is selected from the group consisting of Pfu DNA polymerase and *Thermatoga Maritima*.

7. The method of claim 1, wherein said variant of the sequence in step (a) is a V600E mutation of the human BRAF, EGFR, PIK3CA or KRAS gene.

8. The method of claim 1, wherein said first oligonucleotide is SEQ ID NO: 11.

9. The method of claim 1, wherein said second oligonucleotide is selected from the group consisting of SEQ ID NOS: 2, 3, 4, 5, 7, 8, 9, 10, and 17.

10. A method of detecting a desired variant of a target nucleic acid, the target nucleic acid existing in the form of several variant sequences, the method comprising:
(a) providing a reaction mixture in liquid solution that comprises a first oligonucleotide at least partially complementary to one or more variants of the target nucleic acid, and a second oligonucleotide at least partially complementary to one or more variants of the target nucleic acid and has at least one selective nucleotide that is complementary to a corresponding nucleotide in the desired variant of the target nucleic acid but not complementary to the corresponding nucleotide in undesired variants of the target nucleic acid, wherein said selective nucleotide is placed internally of the 3' terminus, and wherein said second oligonucleotide further comprises at least one nucleotide with a base covalently modified at the exocyclic amino group;
(b) hybridizing said first and second oligonucleotides to at least one variant of the target nucleic acid;
(c) providing conditions suitable for the oligonucleotide extension by a nucleic acid polymerase, wherein said polymerase is capable of extending said second oligonucleotide preferentially when said selective nucleotide forms a base pair with the desired variant of the target nucleic acid, and substantially less when said selective nucleotide does not form a base pair with the desired variant of the target nucleic acid;
(d) repeating the sequence of hybridization and extension steps multiple times; and
(e) detecting the products of said oligonucleotide extension, wherein the extension signifies the presence of the desired variant of the target nucleic acid to which the oligonucleotide has a complementary selective nucleotide;
wherein steps (a)-(e) are performed in a homogeneous assay.

11. The method of claim 1, wherein the structures of the at least one nucleotide with a base covalently modified at the exocyclic amino group is selected from the group consisting of:

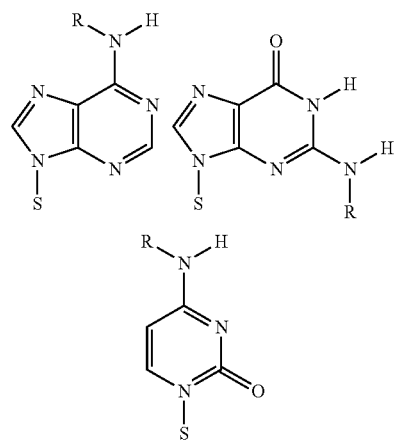

wherein S represents a sugar moiety, and R represents a modifier group.

12. The method of claim 11, wherein the at least one nucleotide with a base covalently modified at the exocyclic amino group occurs at positions -5, -4, -3, -2 -1 relative to the 3'-terminus or at the 3' terminus.

13. The method of claim 12, wherein the base covalently modified at the exocyclic amino group comprises a modifier of the following formula:

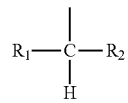

wherein $R_1$ and $R_2$ are independently selected from the group consisting of hydrogen, alkyl, alkoxy, unsubstituted or substituted aryl and phenoxy.

14. The method of claim 13, wherein the modifier has the following formula:

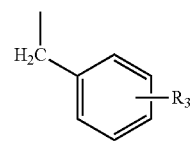

wherein $R_3$ is selected from the group consisting of C1-C6 alkyl, alkoxy and nitro.

15. The method of claim 14, wherein the modifier is selected from the group consisting of:

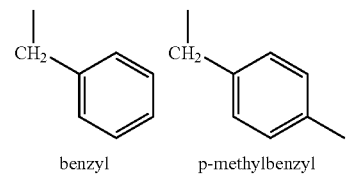

benzyl   p-methylbenzyl

-continued
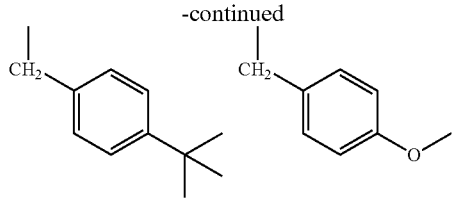
p-tert-butylbenzyl    p-methoxybenzyl
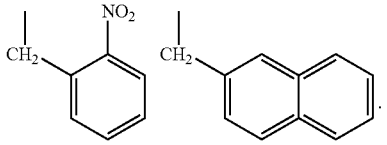
o-nitrobenzyl    2-napthylmethyl
16. The method of claim 11, wherein the base, covalently modified at the exocyclic amino group is selected from a group consisting of $N^6$-benzyl-adenine, $N^6$-para-tert-butyl-benzyl adenine, $N^2$-benzyl-guanine and $N^4$-benzyl-cytosine.
* * * * *

SEQUENCE LISTING

<160> NUMBER OF SEQ ID NOS: 20

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
taaaaatagg tgattttggt ctagctacag aga          33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (29)..(29)
<223> OTHER INFORMATION: N6-para-tert-butyl-benzyl-dA

<400> SEQUENCE: 2
taaaaatagg tgattttggt ctagctacag aga          33

<210> SEQ ID NO 3
<211> LENGTH: 33
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: N6-para-tert-butyl-benzyl-dA

<400> SEQUENCE: 3
taaaaatagg tgattttggt ctagctacag aga                                33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(33)
<223> OTHER INFORMATION: N6-benzyl-dA

<400> SEQUENCE: 4
taaaaatagg tgattttggt ctagctacag aga                                33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(29)
<223> OTHER INFORMATION: N6-para-tert-butyl-benzyl-dA
<220> FEATURE:
<221> NAME/KEY: modified_base
<222> LOCATION: (33)..(33)
<223> OTHER INFORMATION: N6-para-tert-butyl-benzyl-dA

<400> SEQUENCE: 5
taaaaatagg tgattttggt ctagctacag aga                                33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtaaaaatag gtgattttgg tctagctaca gag                                33

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (32)..(32)
<223> OTHER INFORMATION: N6-para-tert-butyl-benzyl-dA

<400> SEQUENCE: 7
gtaaaaatag gtgattttgg tctagctaca gag                                33
```

```
<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: N6-para-tert-butyl-benzyl-dA

<400> SEQUENCE: 8
gtaaaaatag gtgatttggg tctagctaca gag                                   33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: N6-para-tert-butyl-benzyl-dA
<220> FEATURE:
<221> NAME/KEY: modified_base
<222> LOCATION: (32)..(32)
<223> OTHER INFORMATION: N6-para-tert-butyl-benzyl-dA

<400> SEQUENCE: 9
gtaaaaatag gtgatttggg tctagctaca gag                                   33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(29)
<223> OTHER INFORMATION: N6-para-tert-butyl-benzyl-dC
<220> FEATURE:
<221> NAME/KEY: modified_base
<222> LOCATION: (32)..(32)
<223> OTHER INFORMATION: N6-para-tert-butyl-benzyl-dA

<400> SEQUENCE: 10
gtaaaaatag gtgatttggg tctagctaca gag                                   33

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-benzyl-dA

<400> SEQUENCE: 11
tagcctcaat tcttaccatc cacaa                                            25

<210> SEQ ID NO 12
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agtaaaaata ggtgattttg gtctagctac aga                               33

<210> SEQ ID NO 13
<211> LENGTH: 65
<212> TYPE: DNA
<213> ORGANISM: Artificial Sequence
<220> FEATURE:
<223> OTHER INFORMATION: Description of Artificial Sequence: Synthetic
      primer-probe

<400> SEQUENCE: 13
cccgcgcgga cccactccat cgagagcgcg ggagtaaaaa taggtgattt tggtctagct   60
acaga                                                              65

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: N6-para-tert-butyl-benzyl-dA

<400> SEQUENCE: 14
agtaaaaata ggtgattttg gtctagctac aga                               33

<210> SEQ ID NO 15
<211> LENGTH: 65
<212> TYPE: DNA
<213> ORGANISM: Artificial Sequence
<220> FEATURE:
<223> OTHER INFORMATION: Description of Artificial Sequence: Synthetic
      primer-probe
<220> FEATURE:
<221> NAME/KEY: modified_base
<222> LOCATION: (63)..(63)
<223> OTHER INFORMATION: N6-para-tert-butyl-benzyl-dA

<400> SEQUENCE: 15
cccgcgcgga cccactccat cgagagcgcg ggagtaaaaa taggtgattt tggtctagct   60
acaga                                                              65

<210> SEQ ID NO 16
<211> LENGTH: 65
<212> TYPE: DNA
<213> ORGANISM: Artificial Sequence
<220> FEATURE:
<223> OTHER INFORMATION: Description of Artificial Sequence: Synthetic
      primer-probe

<400> SEQUENCE: 16
cccgcgcgga cccactccat cgagagcgcg gggtaaaaat aggtgatttt ggtctagcta   60
cagag                                                              65

<210> SEQ ID NO 17
```

```
<211> LENGTH: 65
<212> TYPE: DNA
<213> ORGANISM: Artificial Sequence
<220> FEATURE:
<223> OTHER INFORMATION: Description of Artificial Sequence: Synthetic
      primer-probe
<220> FEATURE:
<221> NAME/KEY: modified_base
<222> LOCATION: (62)..(62)
<223> OTHER INFORMATION: N6-para-tert-butyl-benzyl-dA
<220> FEATURE:
<221> NAME/KEY: modified_base
<222> LOCATION: (64)..(64)
<223> OTHER INFORMATION: N6-para-tert-butyl-benzyl-dA

<400> SEQUENCE: 17
cccgcgcgga cccactccat cgagagcgcg gggtaaaaat aggtgatttt ggtctagcta      60
cagag                                                                 65

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tctcgatgga gtgggtcc                                                   18

<210> SEQ ID NO 19
<211> LENGTH: 110
<212> TYPE: DNA
<213> ORGANISM: Homo sapiens

<400> SEQUENCE: 19
agtaaaaata ggtgattttg gtctagctac agagaaatct cgatggagtg ggtcccatca     60
gtttgaacag ttgtctggat ccattttgtg gatggtaaga attgaggcta               110

<210> SEQ ID NO 20
<211> LENGTH: 110
<212> TYPE: DNA
<213> ORGANISM: Homo sapiens

<400> SEQUENCE: 20
agtaaaaata ggtgattttg gtctagctac agtgaaatct cgatggagtg ggtcccatca     60
gtttgaacag ttgtctggat ccattttgtg gatggtaaga attgaggcta               110
```